US010549067B2

(12) United States Patent
Garcia Molina et al.

(10) Patent No.: US 10,549,067 B2
(45) Date of Patent: Feb. 4, 2020

(54) SYSTEM AND METHOD FOR ADJUSTING SLOW WAVE DETECTION CRITERIA (71) Applicant: KONINKLIJKE PHILIPS N.V., Eindhoven (NL)

(72) Inventors: Gary Nelson Garcia Molina, Madison, WI (US); Anandi Mahadevan, Murrysville, PA (US); Jesse Salazar, Pittsburgh, PA (US); Surya Subrahmanya Sreeram Vissapragada Venkata Satya, Monroeville, PA (US); John Gerthoffer, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 418 days.

(21) Appl. No.: 15/533,558

(22) PCT Filed: Dec. 11, 2015

(86) PCT No.: PCT/IB2015/059536
§ 371 (c)(1),
(2) Date: Jun. 6, 2017

(87) PCT Pub. No.: WO2016/092515
PCT Pub. Date: Jun. 16, 2016

(65) Prior Publication Data
US 2017/0361060 A1    Dec. 21, 2017

Related U.S. Application Data (60) Provisional application No. 62/090,633, filed on Dec. 11, 2014.

(51) Int. Cl.
*A61M 21/02*    (2006.01)
*A61B 5/00*    (2006.01)
(Continued)

(52) U.S. Cl.
CPC ............ *A61M 21/02* (2013.01); *A61B 5/0484* (2013.01); *A61B 5/4812* (2013.01);
(Continued)

(58) Field of Classification Search
CPC .......... A61M 21/02; A61M 2021/0016; A61M 2021/0022; A61M 2021/0027;
(Continued)

(56) References Cited

U.S. PATENT DOCUMENTS 3,498,287 A    3/1970  Ertl
8,029,431 B2   10/2011 Tononi
(Continued)

FOREIGN PATENT DOCUMENTS

WO    2013179048 A1   12/2013
WO    2014118654 A1    8/2014

OTHER PUBLICATIONS

G. Tononi and C. Cirelli, "Sleep and the price of plasticity: from synaptic and cellular homeostasis to memory consolidation and integration.," Neuron, vol. 81, No. 1, pp. 12-34, Jan. 2014.
(Continued)

*Primary Examiner* — Kaylee R Wilson (57) ABSTRACT

The present disclosure pertains to a system configured to a system configured to detect slow waves based on adjusted slow wave detection criteria and time delivery of the sensory stimulation to correspond to slow waves detected based on the adjusted criteria. The system is configured to adjust slow wave detection criteria to enhance detection of slow waves in a subject. Slow wave detection using adjustable slow wave detection criteria produces more stimulation relative to prior art systems because more individual stimuli are provided if more slow waves are detected. In some embodiments, the system includes one or more of a sensory
(Continued)

stimulator, a sensor, a processor, electronic storage, a user interface, and/or other components.

9 Claims, 9 Drawing Sheets

(51) Int. Cl.
  *A61B 5/0484* (2006.01)
  *A61M 21/00* (2006.01)
(52) U.S. Cl.
  CPC .......... *A61M 2021/0016* (2013.01); *A61M 2021/0022* (2013.01); *A61M 2021/0027* (2013.01); *A61M 2230/10* (2013.01)
(58) Field of Classification Search
  CPC ...... A61M 2230/10; A61M 2021/0044; A61M 2021/0055; A61M 2205/332; A61M 2205/3375; A61M 2205/505; A61M 2205/581; A61M 2205/582; A61M 2205/583; A61M 2230/06; A61M 2230/42; A61M 2230/63; A61B 5/0484; A61B 5/4812; A61B 5/048
  See application file for complete search history.

(56) References Cited

U.S. PATENT DOCUMENTS

| | | |
|---|---|---|
| 8,423,130 B2 | 4/2013 | Thrower et al. |
| 2012/0251989 A1 | 10/2012 | Wetmore et al. |
| 2013/0345522 A1 | 12/2013 | Sun et al. |
| 2014/0057232 A1 | 2/2014 | Anderson |
| 2014/0221779 A1 | 8/2014 | Schoonover |

OTHER PUBLICATIONS

B. A. Riedner, B. K. Hulse, F Ferrarelli, S. Sarasso, and G. Tononi, "Enhancing sleep slow waves with natural stimuli," Medicamundi, vol. 45, No. 2, pp. 82-88, 2010.

H.-V. V Ngo, T. Martinetz, J. Born, and M. Molle, "Auditory Closed-Loop Stimulation of the Sleep Slow Oscillation Enhances Memory," Neuron, vol. 78, No. May, pp. 1-9, 2013.

SYSTEM AND METHOD FOR ADJUSTING SLOW WAVE DETECTION CRITERIA

CROSS-REFERENCE TO PRIOR APPLICATIONS

This application is the U.S. National Phase application under 35 U.S.C. § 371 of International Application Serial No. PCT/IB2015/059536, filed on 11 Dec. 2015, which claims the benefit of U.S. Provisional Application No. 62/090,633, filed on 11 Dec. 2014. These applications are hereby incorporated by reference herein.

BACKGROUND

1. Field

The present disclosure pertains to a system and method for adjusting slow wave detection criteria.

2. Description of the Related Art

Systems for monitoring sleep are known. Known systems detect sleep stages in a subject during a sleep session. The detected sleep stages include stages that correspond to slow wave sleep. Typically, slow wave sleep is detected based on fixed slow wave detection parameters.

SUMMARY

Accordingly, one or more aspects of the present disclosure relate to a system configured to adjust criteria for detecting slow waves in a subject and deliver sensory stimuli with a timing that corresponds to detected slow waves. The system comprises one or more sensory stimulators, one or more sensors, one or more physical computer processors, and/or other components. The one or more sensory stimulators are configured to provide sensory stimuli to the subject during the sleep session. The one or more sensors are configured to generate output signals conveying information related to brain activity of the subject. The one or more physical computer processors are configured by computer readable instructions to obtain criteria for detecting whether the slow waves are present in the subject; determine that the subject is in slow wave sleep by detecting a first slow wave based on the output signals and the obtained criteria; adjust the obtained criteria to enhance detection of subsequent slow waves in the subject; detect a second slow wave based on the output signals and the adjusted criteria; and control the one or more sensory stimulators to deliver the sensory stimuli with a timing that corresponds to detection of the first slow wave and detection of the second slow wave.

Another aspect of the present disclosure relates to a method for adjusting criteria for detecting slow waves in a subject and delivering sensory stimuli with a timing that corresponds to detected slow waves with an adjustment system. The adjustment system comprises one or more sensory stimulators, one or more sensors, and one or more physical computer processors. The method comprises generating, with the one or more sensors, output signals conveying information related to brain activity of the subject; obtaining, with the one or more physical computer processors, criteria for detecting whether the slow waves are present in the subject; determining, with the one or more physical computer processors, that the subject is in slow wave sleep by detecting a first slow wave based on the output signals and the obtained criteria; adjusting, with the one or more physical computer processors, the obtained criteria to enhance detection of subsequent slow waves in the subject; detecting, with the one or more physical computer processors, a second slow wave based on the output signals and the adjusted criteria; and controlling, with the one or more physical computer processors, the one or more sensory stimulators to deliver the sensory stimuli with a timing that corresponds to detection of the first slow wave and detection of the second slow wave.

Still another aspect of present disclosure relates to a system configured to adjust criteria for detecting slow waves in a subject and deliver sensory stimuli with a timing that corresponds to detected slow waves. The system comprises means for providing sensory stimuli to the subject during the sleep session; means for generating output signals conveying information related to brain activity of the subject; means for obtaining criteria for detecting whether the slow waves are present in the subject; means for determining that the subject is in slow wave sleep by detecting a first slow wave based on the output signals and the obtained criteria; means for adjusting the obtained criteria to enhance detection of subsequent slow waves in the subject; means for detecting a second slow wave based on the output signals and the adjusted criteria; and means for controlling the means for providing sensory stimuli to deliver the sensory stimuli with a timing that corresponds to detection of the first slow wave and detection of the second slow wave.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
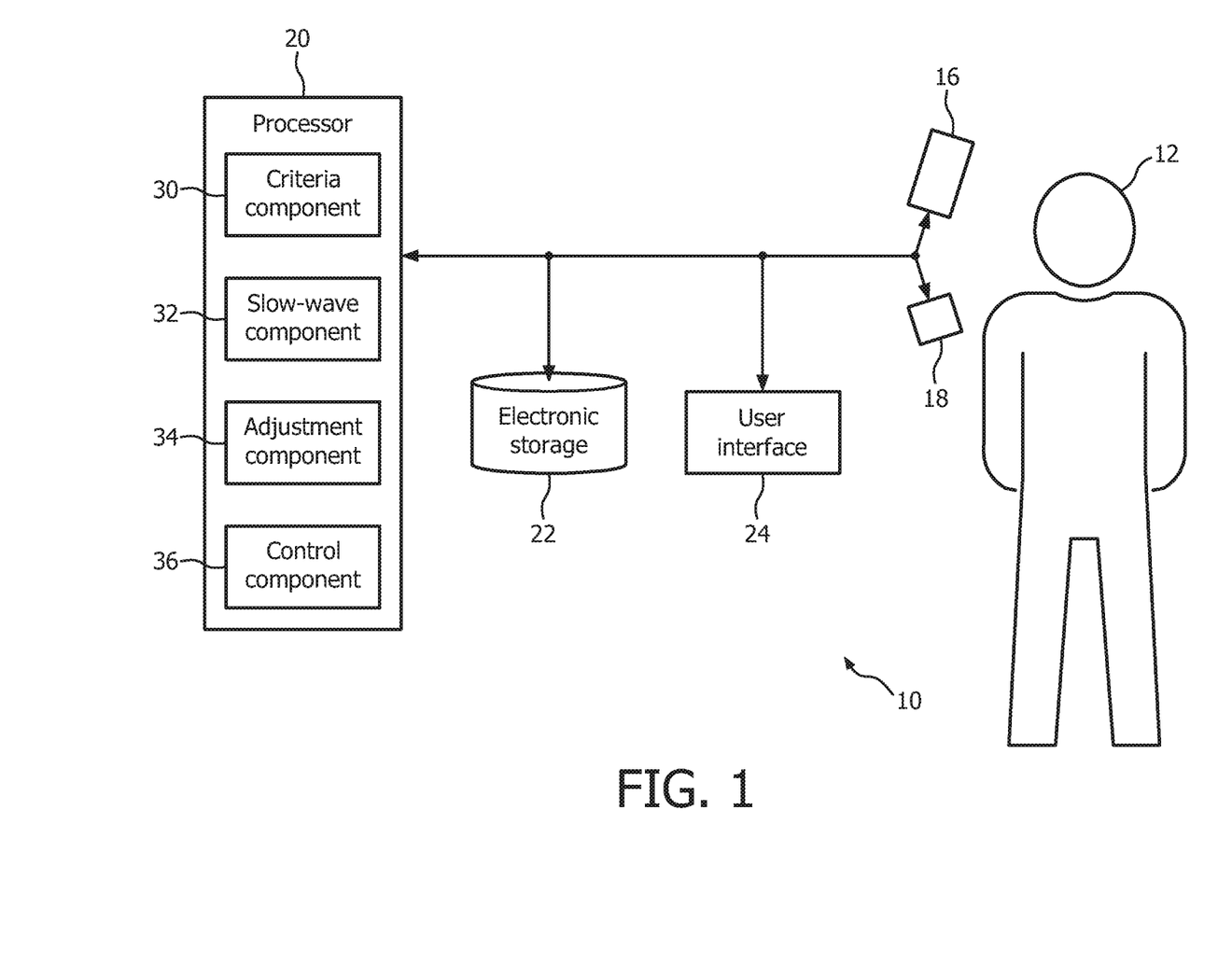
FIG. 1 is a schematic illustration of a system configured to adjust criteria for detecting slow waves in a subject and deliver sensory stimuli with a timing that corresponds to detected slow waves.

FIG. 1 is a schematic illustration of a system 10 configured to adjust criteria for detecting slow waves in a subject 12 and deliver sensory stimuli with a timing that corresponds to detected slow waves. The restorative value of sleep may be enhanced by increasing the amount and/or the amplitude of slow waves that are present in subject 12 during deep sleep (e.g., stage N3 sleep described below). This translates into an increase in slow wave activity (e.g., EEG power in the 0.5 to 4 Hz frequency band). Slow waves may be enhanced through sensory (e.g., auditory) stimulation during deep (and/or other non-REM) sleep. Parameters of the sensory stimulation (e.g., timing, intensity, etc.) may be adjusted to facilitate enhancement of slow waves, prevent arousals in subject 12, and/or for other reasons. Typically, individual sensory stimuli are timed to correspond to detection of individual slow waves. Slow wave detection using fixed slow wave detection criteria leads to a relatively low amount of stimulation because few individual stimuli are provided if few slow waves are detected based on the fixed criteria.

System 10 is configured to detect slow waves based on adjusted slow wave detection criteria and time delivery of the sensory stimulation to correspond to slow waves detected based on the adjusted criteria. System 10 is configured to adjust slow wave detection criteria to enhance detection of slow waves in subject 12. Slow wave detection using adjustable slow wave detection criteria produces more stimulation relative to prior art systems because more individual stimuli are provided if more slow waves are detected. System 10 is configured to dynamically adjust slow wave detection criteria for a sleep session based on the position of a slow wave in a set of slow waves (e.g., detection criteria is adjusted to enhance detection of subsequent slow waves that occur after a first slow wave in the set of slow waves), based on a sleep cycle of subject 12 (e.g., detection criteria is adjusted to enhance detection of slow waves that occur during a second sleep cycle relative to slow waves that occur during a first sleep cycle), and/or based on other information. In some embodiments, system 10 includes one or more of a sensory stimulator 16, a sensor 18, a processor 20, electronic storage 22, a user interface 24, and/or other components.

Sensory stimulator 16 is configured to provide sensory stimuli to subject 12. Sensory stimulator 16 is configured to provide sensory stimulation to subject 12 prior to a sleep session, during a sleep session, and/or at other times. For example, sensory stimulator 16 may be configured to provide sensory stimuli to subject 12 to induce deeper sleep in subject 12, maintain sleep in a specific sleep stage during the sleep session, during deep (e.g., slow wave sleep) sleep in a sleep session, to facilitate a transition to a lighter stage of sleep, and/or for other reasons and/or at other times. In some embodiments, sensory stimulator 16 may be configured to induce, increase, enhance, maintain, and/or decrease sleep slow waves in subject 12. Sensory stimulator 16 is configured to facilitate non-invasive brain stimulation and/or other stimulation. Sensory stimulator 16 may be configured to facilitate non-invasive brain stimulation using the sensory stimuli. The sensory stimuli include odors, sounds, visual stimulation, touches, tastes, somato-sensory stimulation, haptic, and/or other stimuli. For example, sensory stimulator 16 may be configured to provide acoustic tones to subject 12. Examples of sensory stimulator 16 may include one or more of a music player, a tone generator, a collection of electrodes on the scalp of subject 12, a unit to deliver vibratory stimulation, a coil generating a magnetic field to directly stimulate the brain's cortex, light generators, a fragrance dispenser, and/or other devices. In some embodiments, sensory stimulator 16 is configured to adjust the timing, intensity, and/or other characteristics of the stimulation provided to subject 12.

Sensor 18 is configured to generate output signals conveying information related to brain activity of subject 12. The brain activity of subject 12 may correspond to a current sleep stage of subject 12. The current sleep stage of subject 12 may be associated with rapid eye movement (REM) sleep, non-rapid eye movement (NREM) sleep, and/or other sleep. The current sleep stage of subject 12 may be one or more of NREM stage N1, stage N2, or stage N3 sleep, REM sleep, and/or other sleep stages. In some embodiments, NREM stage 3 or stage 2 sleep may be slow wave sleep. Sensor 18 may comprise one or more sensors that measure such parameters directly. For example, sensor 18 may include electroencephalogram (EEG) electrodes configured to detect electrical activity along the scalp of subject 12 resulting from current flows within the brain of subject 12. Sensor 18 may comprise one or more sensors that generate output signals conveying information related to brain activity of subject 12 indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. Although sensor 18 is illustrated at a single location near subject 12, this is not intended to be limiting. Sensor 18 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16), or processor 20 may represent processing functionality of a plurality of devices operating in coordination.

As shown in FIG. 1, processor 20 is configured to execute one or more computer program components. The one or more computer program components may comprise one or more of a criteria component 30, a slow wave component 32, an adjustment component 34, a control component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Criteria component 30 is configured to obtain criteria for detecting whether slow waves are present in subject 12. Criteria component 30 is configured to obtain the slow wave detection criteria from information entered and/or selected by a user (e.g., subject 12, a doctor, a caregiver, etc.) via user interface 24, information programmed at manufacture, information from previous sleep sessions of subject 12, and/or other sources of information. In some embodiments, the slow wave detection criteria are associated with an EEG voltage signal for the sleep session of subject 12. In some embodiments, the obtained slow wave detection criteria may include criteria associated with EEG voltage, EEG voltage zero crossings, time between EEG voltage zero crossings, slow wave amplitude (e.g., negative peak voltage, positive peak voltage) criteria, and/or other criteria. For example, criteria component 30 may obtain slow wave detection criteria indicating that slow waves should be detected responsive to a negative peak (and/or the absolute value of the negative peak) of an EEG voltage falling below about −40 µV (and/or exceeding an absolute value of about 40 µV). This is further described below with respect to FIG. 2.

Slow wave component 32 is configured to detect slow wave sleep (e.g., stage N3 sleep) in subject 12. Slow wave component 32 is configured to detect slow wave sleep in subject 12 based on the output signals from sensors 18, the obtained criteria, and/or based on other information. In some embodiments, slow wave component 32 may detect slow wave sleep in subject 12 based on an analysis of the information conveyed by the output signals. The analysis may include generating and/or monitoring an EEG during a sleep session of subject 12. In some embodiments, the analysis may include detecting slow wave sleep based on a ratio characterizing the depth of sleep. In some embodiments, the ratio may be:

$$\rho = \log\left(\frac{\beta}{\delta}\right),$$

where β and δ represent a power in a beta band (e.g., usually defined as the power in the frequency range 15-30 Hz although variations in limits of the range are very common) of the EEG and a delta band (usually defined as the power in the frequency range 0.5-4.5 Hz although, just as in the case of the beta band, there is no standard definition of the frequency limits) of the EEG respectively. In some embodiments, slow wave component 32 is configured to identify slow wave sleep in subject 12 responsive to an instantaneous slow wave sleep ratio ρ(t), estimated based on instantaneous powers β(t) and δ(t), staying below a threshold ratio for longer than a given period of time. In some embodiments, the threshold ratio and/or the given period of time may be determined based on previous sleep sessions of subject 12, and/or other information. In some embodiments, the threshold ratio and/or the given period of time may be programmed at manufacture. For example, the threshold ratio and/or the given period of time may be programmed at manufacture based on empirically accepted values such as a threshold ratio of about −2, and/or a given period of time of about 2 minutes.

Slow wave component 32 is configured such that detecting slow wave sleep includes detecting individual slow waves in subject 12. The individual slow waves are detected based on the output signals, an analysis of the output signals (e.g., an EEG), the obtained criteria, and/or other information. In some embodiments, detecting individual slow waves may be performed in real-time or near real-time during a sleep session of subject 12. In some embodiments, slow wave component 32 is configured to detect individual slow waves by analyzing a shape and/or other features of an EEG voltage signal and then comparing the shape and/or other features to the obtained criteria. Slow waves may be detected responsive to the shape and/or other features of the EEG voltage signals satisfying the obtained criteria.

Figure 2:
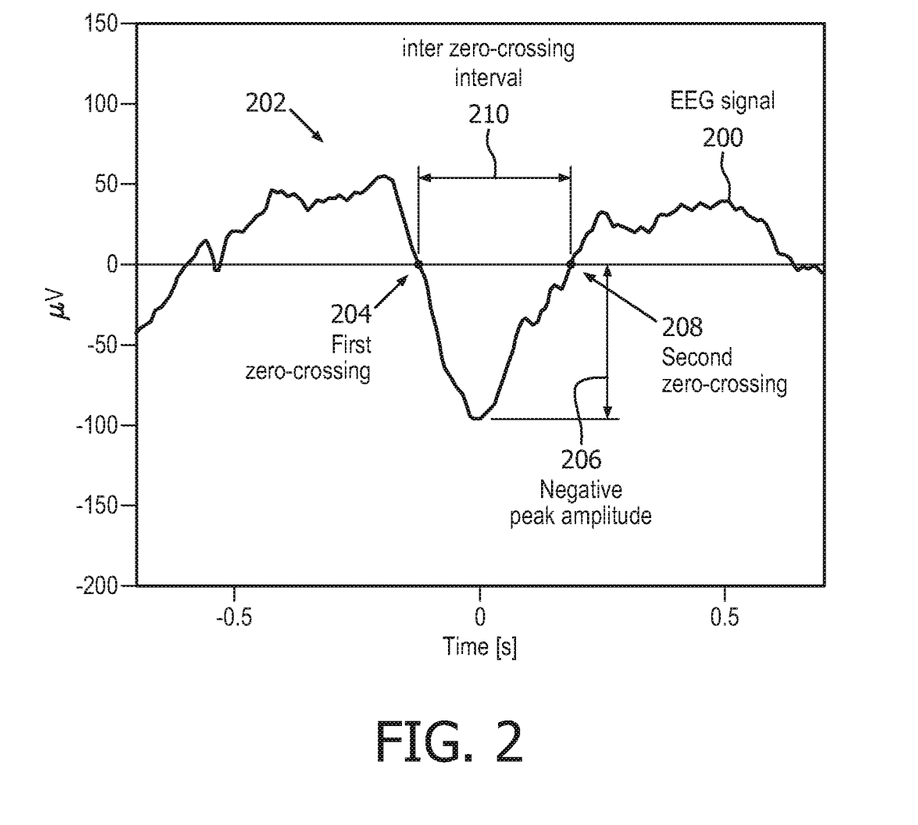
FIG. 2 illustrates detecting an individual slow wave based on an EEG voltage signal.

By way of a non-limiting example, FIG. 2 illustrates detecting an individual slow wave 202 based on an EEG voltage signal 200. Slow wave component 32 (FIG. 1) detects slow wave 202 by detecting negative-going zero-crossing 204 and comparing the amplitude of the most prominent negative peak 206 following the first zero-crossing to obtained slow wave detection criteria for negative peak 206 amplitude (e.g. a threshold of −40 µV). If the value of the amplitude of the negative peak satisfies the criteria (e.g., exceeds the threshold), then the positive-going zero-crossing 208 is detected. If the duration of time 210 between zero-crossings 204 and 208 satisfies criteria for time duration 210 (e.g., from 200 milliseconds to 800 milliseconds), then slow wave 202 is detected.

Returning to FIG. 1, in some embodiments, slow wave component 32 is configured to identify sleep stages in addition to, and/or instead of slow wave sleep. For example, slow wave component 32 is configured to identify NREM stage N1, stage N2, or stage N3 sleep, REM sleep, and/or other sleep stages. In some embodiments, slow wave component 32 is configured to detect arousals in subject 12. Slow wave component 32 determines a likelihood of arousal of subject 12 based on EEG power in high frequency bands (e.g., alpha: 8-12 Hz, beta: 15-30 Hz).

Adjustment component 34 is configured to adjust the obtained criteria to enhance detection of slow waves in subject 12. In some embodiments, the criteria may be adjusted following one or more individual detections of slow waves in a series of consecutive slow waves. For example, adjustment component 34 may adjust the obtained criteria after detection of a first slow wave and then maintain the same adjusted criteria for subsequent slow waves in the series of slow waves. As another example, adjustment component 34 may adjust the criteria after every individual slow wave detection. In some embodiments, the criteria may be adjusted during other series of slow waves that occur during later sleep cycles of subject 12 during the sleep session. For example, adjustment component 34 is configured to adjust the obtained criteria after detection of a first slow wave and then again after detection a second slow wave that immediately follows the first slow wave (within the same sleep cycle). As another example, adjustment component 34 is configured to adjust the criteria after a first slow wave that is a leading slow wave in a first sleep cycle of subject 12 and then again after detection of a second slow wave that is a leading slow wave in a second sleep cycle of subject 12.

Adjusting the criteria to enhance detection of slow waves includes adjusting the criteria to make slow waves easier to detect. Adjusting the criterial may include adjusting criteria associated with EEG voltage, EEG voltage zero crossings, time between EEG voltage zero crossings, slow wave amplitude (e.g., negative peak voltage, positive peak voltage) criteria, and/or other criteria. For example, adjustment component 34 may adjust slow wave detection criteria indicating that slow waves should be detected responsive to a negative peak (and/or the absolute value of the negative peak) of an EEG voltage breaching a threshold of about −40 µV (and/or an absolute value of 40 µV) to about −20 µV (and/or an absolute value of 200). As described above, in some embodiments, adjustment component 34 may make this stepped adjustment after a first slow wave (and/or after the first slow waves in multiple sleep cycles), and in some embodiments, adjustment component 34 may make this stepped adjustment after every individual slow wave detection. The amount that individual criterial are adjusted may be determined at manufacture, based on information entered and/or selected via user interface 24, based on information from previous sleep sessions of subject 12, and/or based on other information. The negative peak threshold criteria and the 200 µV step described herein are not intended to be limiting. Adjustment component 34 may adjust any individual criterion by any amount that allows system 10 to function as described herein.

In some embodiments, adjustment component 34 is configured such that the first slow wave detected during stage N3 sleep is detecting using a −40 µV threshold on the negative peak amplitude. For subsequent slow waves the threshold is lowered, for example, to −20 µV (e.g., and/or any other level as described above). If the stimulation ceases (described below) due to an increase in the likelihood of an arousal and/or because the N3 period ends, the same strategy is repeated the next time the stimulation begins (e.g., during slow wave sleep in subsequent sleep cycles).

Figure 3:
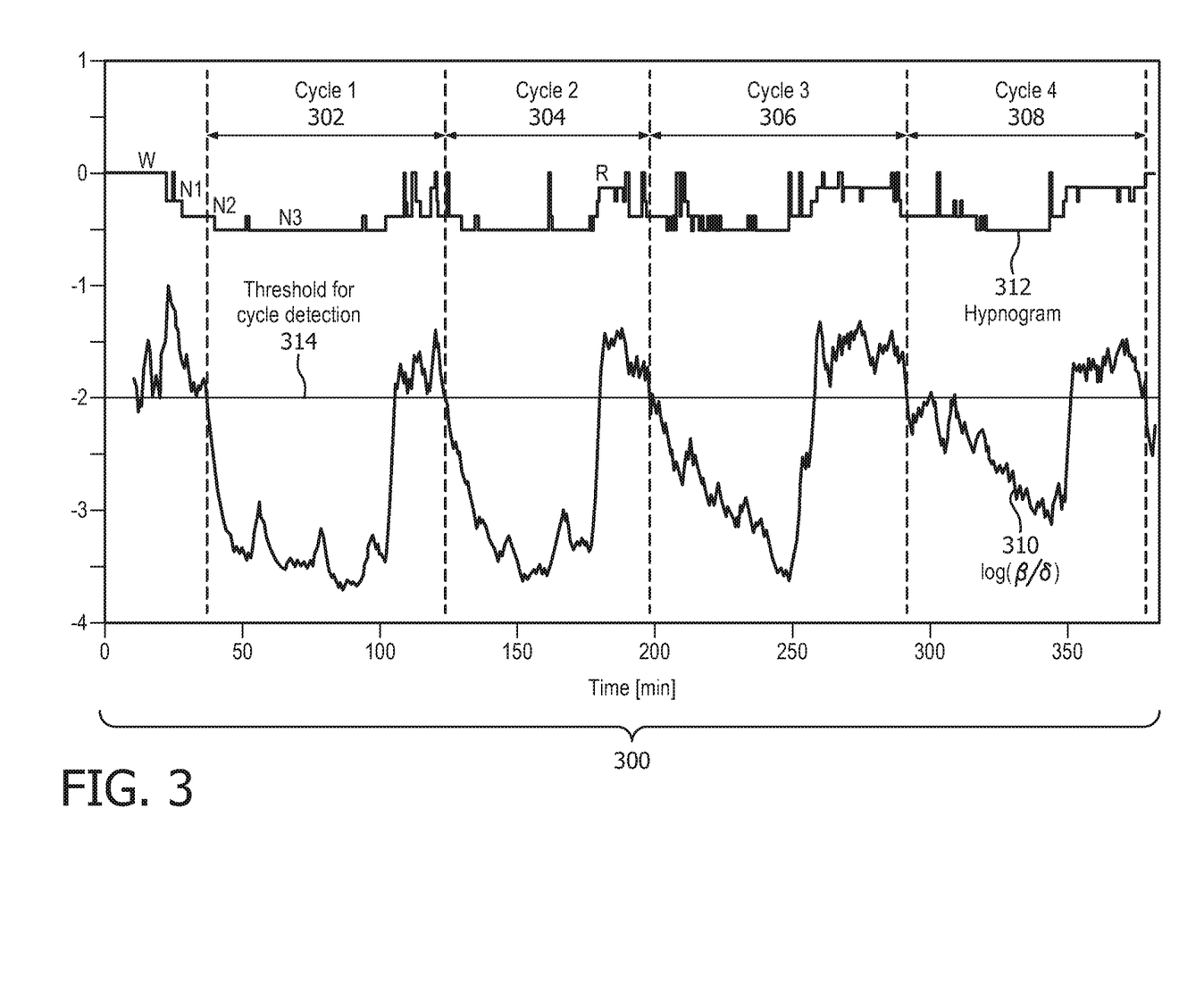
FIG. 3 illustrates four individual sleep cycles detected during a sleep session.

As described above, in some embodiments, adjustment component 34 is configured to adjust the negative peak threshold criteria depending on the sleep cycle. In some embodiments, adjustment component 34 is configured to adjust the negative peak threshold criteria by successive steps of 20 µV, 10 µV, 5 µV, and/or any other amount depending on the sleep cycle. (Using the sleep cycle as a basic time period to adjust the slow wave detection criteria is reasonable because all of the sleep stages are visited in an orderly progression (wake-N1-N2-N3-REM) during an individual sleep cycle). Slow wave component 32 is configured to detect sleep responsive to the ratio log (β/δ) breaching a threshold of −2 on the ratio. In some embodiments, the ration may be log ($\beta_{RMS}/\delta_{RMS}$) where $\beta_{RMS}$ and $\delta_{RMS}$ correspond to the EEG's RMS power in the beta (15-30 Hz) frequency band and in the delta (0.5-4 Hz) frequency band respectively. FIG. 3 illustrates detecting sleep cycles.

FIG. 3 illustrates four individual sleep cycles 302, 304, 306, 308 detected by slow wave component 32 (FIG. 1) during a sleep session 300. In FIG. 3, log (β/δ) 310 is plotted below a corresponding manually scored hypnogram 312. In some embodiments, the individual sleep cycles 302, 304, 306, 308 are detected by slow wave component 32 based on a log (β/δ) threshold 314. In some embodiments, threshold 314 may be determined based on previous sleep sessions of subject 12, and/or other information. In some embodiments, threshold 314 may be set and/or adjusted via user interface 24 (shown in FIG. 1). In some embodiments, threshold 314 may be programmed at manufacture. For example, threshold 314 may be programmed at manufacture based on empirically accepted values such as a threshold of about −2 on the log(β/δ) (illustrated in FIG. 3). In some embodiments, slow wave component 32 is configured to detect individual sleep cycles responsive to log (β/δ) 310 breaching log (β/δ) threshold 314. In some embodiments, slow wave component 32 determines that log (β/δ) 310 breaches log (β/δ) threshold 314 responsive to log (β/δ) 310 staying above and/or below log (β/δ) threshold 314 for longer than a given period of time.

In some embodiments, the criteria is adjusted based on delta activity RMS, an amplitude of one or more previously detected slow waves, and/or other information. In some embodiments, adjustment component 34 is configured to adjust the negative peak threshold criteria and/or other slow wave detection criteria based on the amplitude of the N (for instance N=5) previously detected slow waves (e.g., the amplitude of the slow waves is determined by slow wave component 32 as described above). As in the examples above, adjustment component 34 may be configured such that an initial value of the negative peak threshold criteria is −40 µV (though this is not intended to be limiting). Adjustment component 34 may be configured to average (and/or perform other analysis on) the amplitude of the latest N detected slow waves and then adjust the negative peak threshold criteria to the determined average (and/or other analyzed parameter).

In some embodiments, adjustment component 34 is configured to adjust the negative peak threshold criteria and/or other slow wave detection criteria for blocks of slow waves based on the effect of previously delivered sensory stimulation (e.g., tones). A block of slow waves may occur for example, over a period of about 15 seconds and include about 1 to about 20 slow waves during a sleep cycle. Adjustment component 34 is configured to quantify the effect of previously delivered stimulation by comparing an average delta root mean square (RMS) (e.g., RMS power in the delta (0.5 to 4 Hz) band averaged over a duration of at least about 4 seconds (other durations are contemplated)) for a current block of slow waves to that of one or more previous blocks of slow waves. In some embodiments, adjustment component 34 is configured such that the negative peak threshold criteria and/or other slow wave detection criteria is adjusted by for instance −5 μV (e.g., increasing the detection specificity) if the delta RMS increases. This may reduce false detections because it is reasonable to assume that large amplitude slow waves are occurring because the delta RMS increases. If delta RMS decreases, adjustment component 34 is configured such that the negative peak threshold criteria and/or other slow wave detection criteria is adjusted by for instance +5 μV (increasing the detection sensitivity and also increasing the amount of stimulation). In some embodiments, adjustment component 34 is configured to adjust the negative peak threshold criteria and/or other slow wave detection criteria for blocks of slow waves with a step size of about +5 μV (which increases the slow wave detection sensitivity) while ensuring that the average amplitude of slow waves in these blocks increases due to stimulation (this can increase the amplitude of smaller slow waves). Since stimulating on lower amplitude slow waves may potentially cause arousals, when arousals are detected (e.g., by slow wave component 32 using the alpha and beta band passed filtered EEG signal), adjustment component 34 adjusts the slow wave detection criteria back to starting levels to ensure stimulation does not induce arousals (e.g., by minimizing stimulation opportunity because less slow waves are detected). This is illustrated in FIG. 4.

Figure 4:
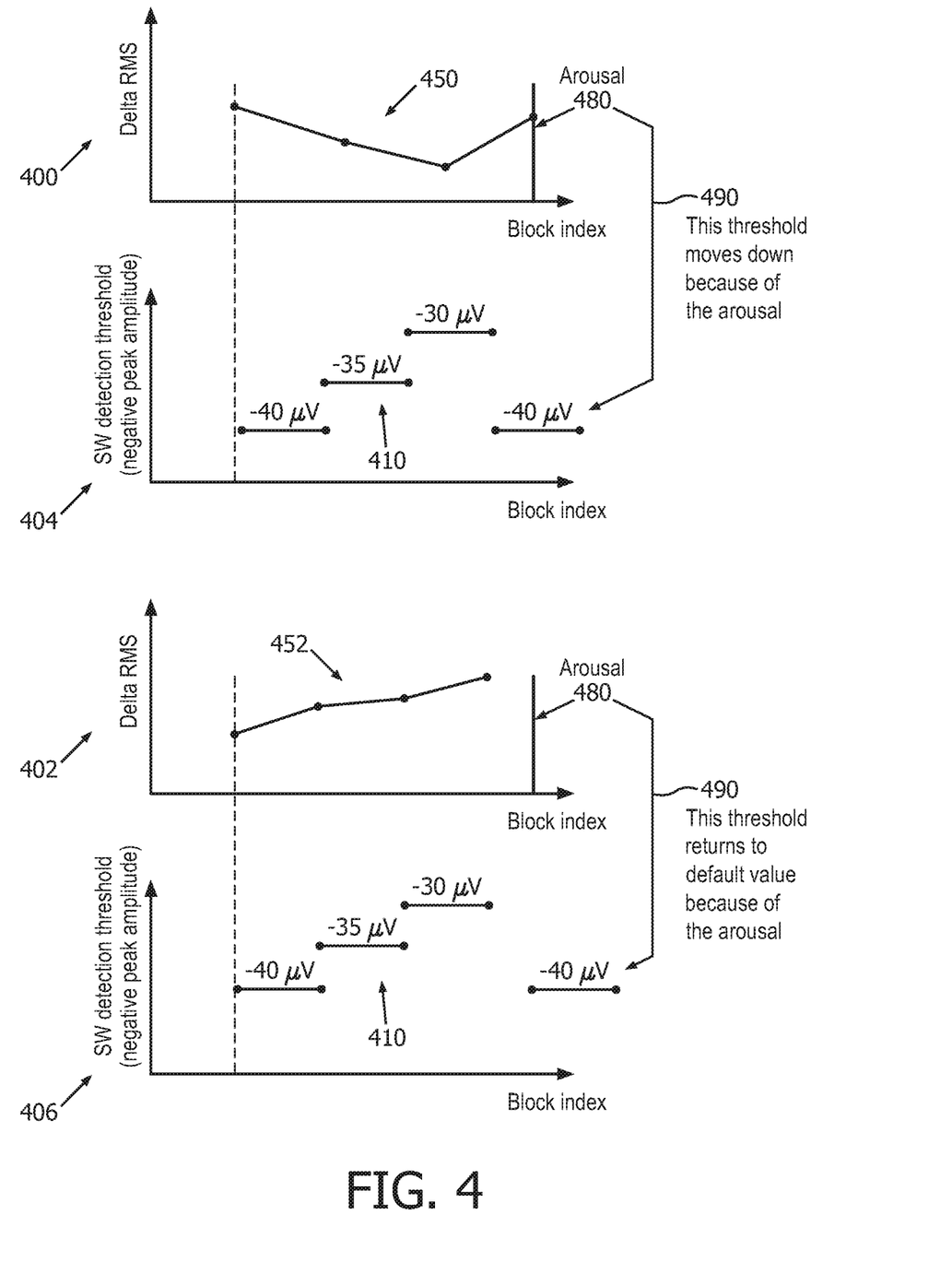
FIG. 4 illustrates delta RMS versus block index curves and negative peak amplitude threshold criteria versus block index curves.

FIG. 4 illustrates delta RMS versus block index curves 400, 402 and negative peak amplitude threshold criteria versus block index curves 404, 406. Curves 400, 402, 404, and 406 illustrate increasing 410 the negative peak threshold criteria by (e.g., by +5 μV) when the delta RMS decreases 450 in the case of curve 400 and increases in the case of curve 402. Adjustment component 34 (FIG. 1) may be configured to increase 410 the negative peak threshold criteria by (e.g., by +5 μV) when the delta RMS decreases 450 to increase sensitivity to slow waves so that more slow waves are detected. Adjustment component 34 (FIG. 1) may be configured to increase 410 the negative peak threshold criteria by (e.g., by +5 μV) when the delta RMS increases 452 to increase sensitivity to smaller amplitude slow waves that are present among larger amplitude slow waves in the same block of slow waves. When arousals are detected 480, adjustment component 34 adjusts 490 the slow wave detection criteria such that the negative peak threshold criteria increases in absolute value to ensure stimulation does not induce arousals. In some embodiments, the negative peak threshold criteria is set back to starting levels.

Returning to FIG. 1, control component 36 is configured to control sensory stimulator 16 to deliver sensory stimulation with a timing that corresponds to detection of the slow waves. Control component 36 is configured to control sensory stimulator 16 to deliver sensory stimulation while subject 12 is in stage N3 sleep and/or other deep sleep (e.g., determined by slow wave component 32). Control component 36 is configured to control sensory stimulator 16 to not deliver sensory stimulation responsive to slow wave component 32 determining that an arousal is likely in subject 12. In some embodiments, control component 36 is configured such that timing of the sensory stimulation corresponds to up-states of slow waves such that the more individual slow waves are detected, the more sensory stimulation is delivered, and conversely, the less individual slow waves are detected, the less sensory stimulation is delivered. In some embodiments, the sensory stimulation is in phase stimulation with the timing of the sensory stimulation being set in terms of a time delay from the detection of a slow wave's second zero-crossing to a positive peak of the slow wave. This is illustrated in FIG. 5.

Figure 5:
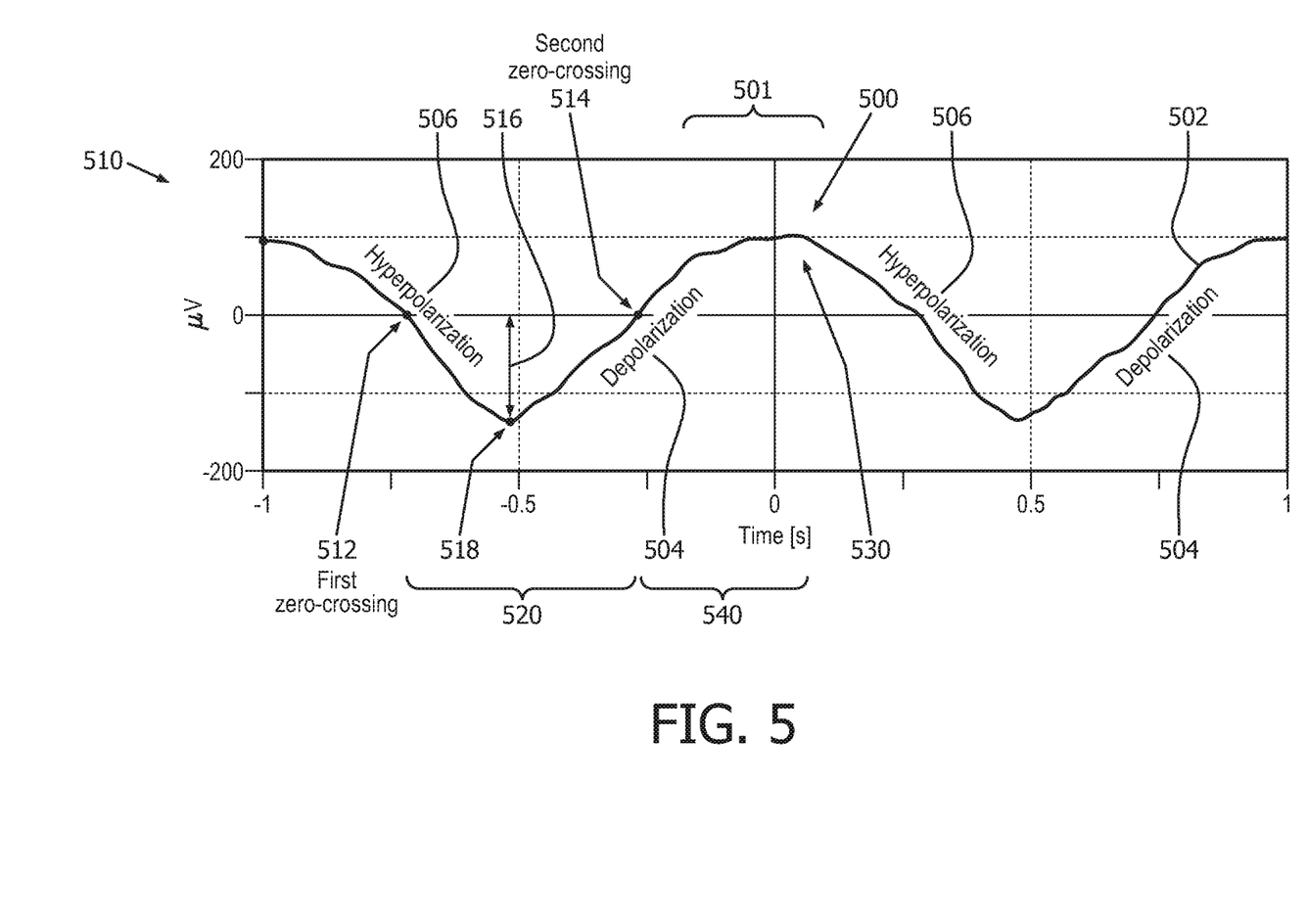
FIG. 5 illustrates stimulation timing for sensory stimulation that coincides with an up-state of a detected slow wave in an EEG voltage signal.

FIG. 5 illustrates stimulation timing 500 for sensory stimulation that coincides with an up-state 501 of a detected slow wave 502 in an EEG voltage signal 510. Slow wave 502 may be detected (as described above related to FIG. 2) based on zero-crossings 512, 514, an amplitude 516 of the most prominent negative peak 518 following zero-crossing 512, a timing 520 between zero crossings 512 and 514, and/or other information. Up-state 501 may be and or correspond to an end of depolarization phase 504. Hyperpolarization phase 506 precedes and/or follows depolarization phase 504. During hyperpolarization phase 506 cortical neurons are deeply hyperpolarized and remain silent for a few hundred milliseconds. A down state is followed by depolarization phase 504 and/or up state 501 that also lasts for several hundred milliseconds. During up-state 501, neurons fire at rates that can be even higher than in quiet wakefulness. Control component 36 is configured such that stimulation is delivered at substantially each detected slow wave provided that the sleep stage of subject 12 (FIG. 1) is N3 and that the likelihood for evoking an arousal is low as quantified by the EEG power in the high frequency bands (determined by slow wave component 32 shown in FIG. 1). In some embodiments, the timing of the sensory stimulation is set in terms of a time delay 540 (e.g., in milliseconds) from the detection of the slow wave's second zero-crossing 514 to a positive peak 530 of slow wave 502. This stimulation timing is referred to as in-phase stimulation.

Returning to FIG. 1, in some embodiments, control component 36 is configured to control sensory stimulator 16 to deliver time-out stimulation responsive to a time-out time after detection of an individual slow wave elapsing without additional slow waves being detected. The time-out stimulation is delivered in an attempt to induce a slow wave that satisfies the adjusted slow wave detection criteria (e.g., an amplitude of the slow wave breaches amplitude threshold criteria). In some embodiments, the time-out time is static. In some embodiments, control component 36 is configured to adjust the time-out time. For example, in embodiments with a static time-out time, time out stimulation is delivered if no slow waves are detected for a period of about 2 (this is not intended to be limiting and could be any static amount of time that allows system 10 to function as described herein) seconds while subject 12 is in deep sleep. In embodiments where the time-out time is adjusted, a timeout period of about 1.2 (again not intended to be limiting) seconds may be used initially for generating timeout tones. If a number of timeout tones played in the previous 20 (for example, not intended to be limiting) seconds does not decrease, this indicates that the sensory stimuli are not generating subsequent slow waves that satisfy adjusted criteria. Thus, control component 36 is configured to incrementally increase the time-out time to reduce the risk of inducing arousals because of minimally effective and/or ineffective timeout tones. If the number of timeout tones played does decrease, then control component is configured to decrease the time-out time (e.g., limited by the minimum of 1.2 seconds).

In some embodiments, system 10 is configured such that a first slow wave is detected using a −40 μV threshold criterion on the negative peak amplitude and the amplitude threshold is lowered to −30 μV if one timeout tone is generated and does not subsequently induce a natural above-threshold slow wave. Subsequently, the threshold may be lowered to −20 μV if a second timeout tone is generated. This threshold may be reset back to −40 μV upon detection (with the reduced threshold) of slow waves with amplitudes below −60 μV (for example) to avoid false-positive stimulation during periods of large-amplitude slow wave sleep.

Figure 6:
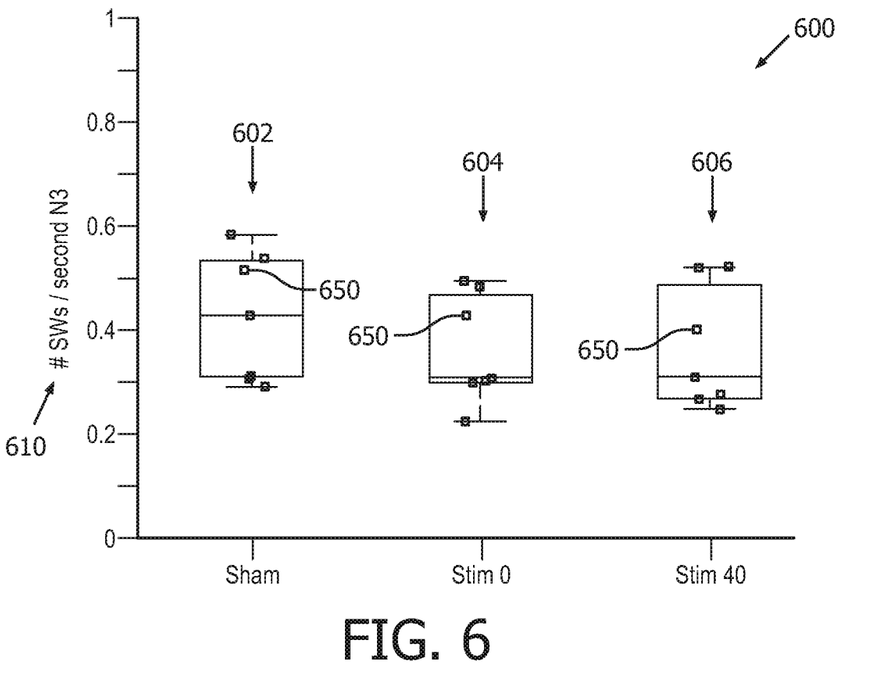
FIG. 6 illustrates experimental data showing the number of slow waves during sleep stage N3 detected without adjusting slow wave detection criteria.

FIG. 6-FIG. 9 illustrate detecting slow waves and delivering sensory stimulation based on static, unchanging slow wave detection criteria (FIG. 6 and FIG. 8) compared to detecting slow waves and delivering sensory stimulation based on adjusted slow wave detection criteria (e.g., system 10). FIG. 6 illustrates experimental data 600 showing the number of slow waves during sleep stage N3 detected without adjusting slow wave detection criteria. The data in FIG. 6 is experimental sleep EEG data from a study involving 7 subjects and a total of 27 overnight recordings: 12 nights without stimulation (referred to as sham 602), 8 nights with stimulation at a 0-millisecond delay (referred to as slim0 604), and 7 nights with stimulation at a 40-millisecond delay (referred to as sham40 606). To account for differences in N3 duration between different nights and subjects, the number of detected slow waves was normalized by the N3 duration in seconds to obtain a slow wave density estimation 610. No statistically significant difference (p=0.1) exists between the conditions 602, 604, 606. On average, 0.38 slow waves were detected per second (standard deviation 0.11). The number of auditory tones (e.g., individual sensory stimuli) per detected slow wave was, on average, 0.67. This implies that, on average, 0.25 (0.38× 0.67) tones per second were delivered using in phase stimulation and without adjusting slow wave detection criteria. Individual dots 650 represent the result of a single sleep session.

Figure 7:
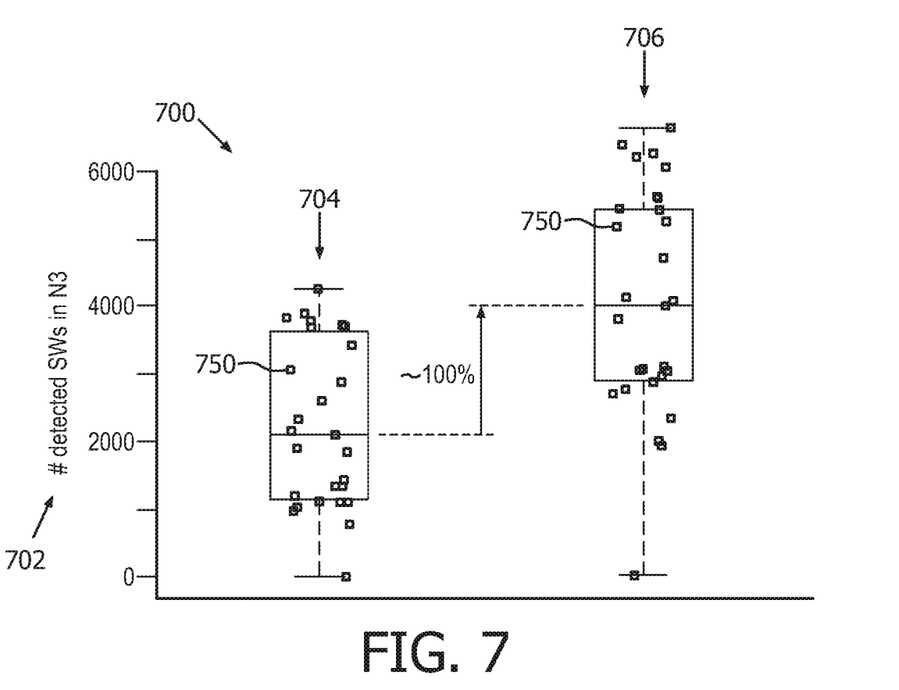
FIG. 7 illustrates experimental data showing the number of slow waves during sleep stage N3 detected using adjusted slow wave detection criteria.

FIG. 7 illustrates experimental data 700 showing the number of slow waves during sleep stage N3 detected using adjusted slow wave detection criteria. FIG. 7 illustrates the number 704 of slow waves 702 detected using static, unchanging negative peak voltage criteria of −40 μV compared to the number 706 of slow waves 702 detected using an adjusted negative peak voltage criteria of −20 μV. By adjusting the detection criteria to −20 μV (e.g., after detection of a first slow wave), system 10 (FIG. 1) achieved an average percent increase in the number of detected slow waves of almost 100%. By considering the empirical result shown in FIG. 6, that on average 0.67 tones are delivered per detected slow wave, system 10 may increase the amount of stimulation by about 67%. Individual dots 750 represent the result of a single sleep session.

Figure 8:
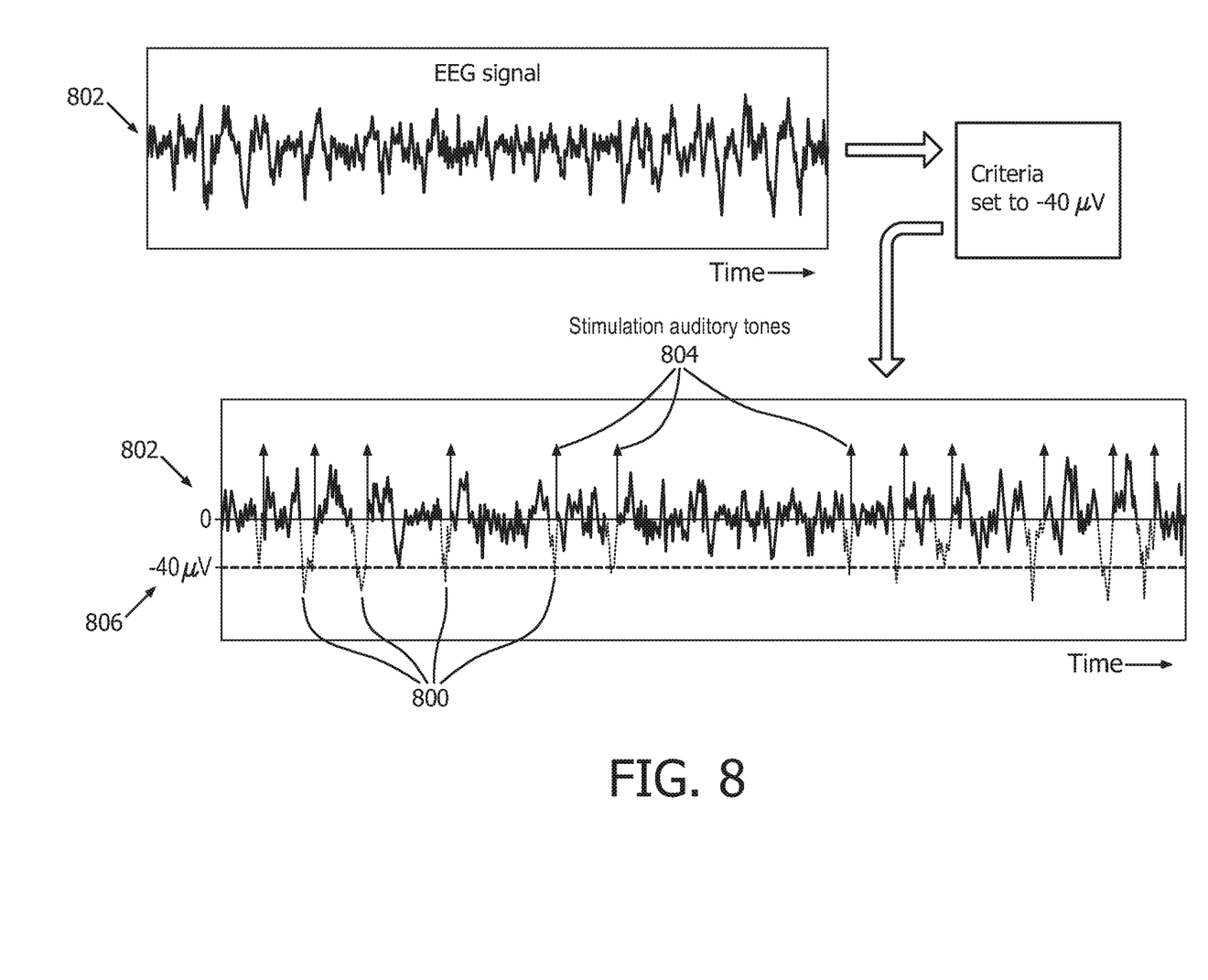
FIG. 8 illustrates detecting slow waves in an EEG voltage signal and corresponding delivery of auditory tones using static, unchanging negative peak voltage criteria.
Figure 9:
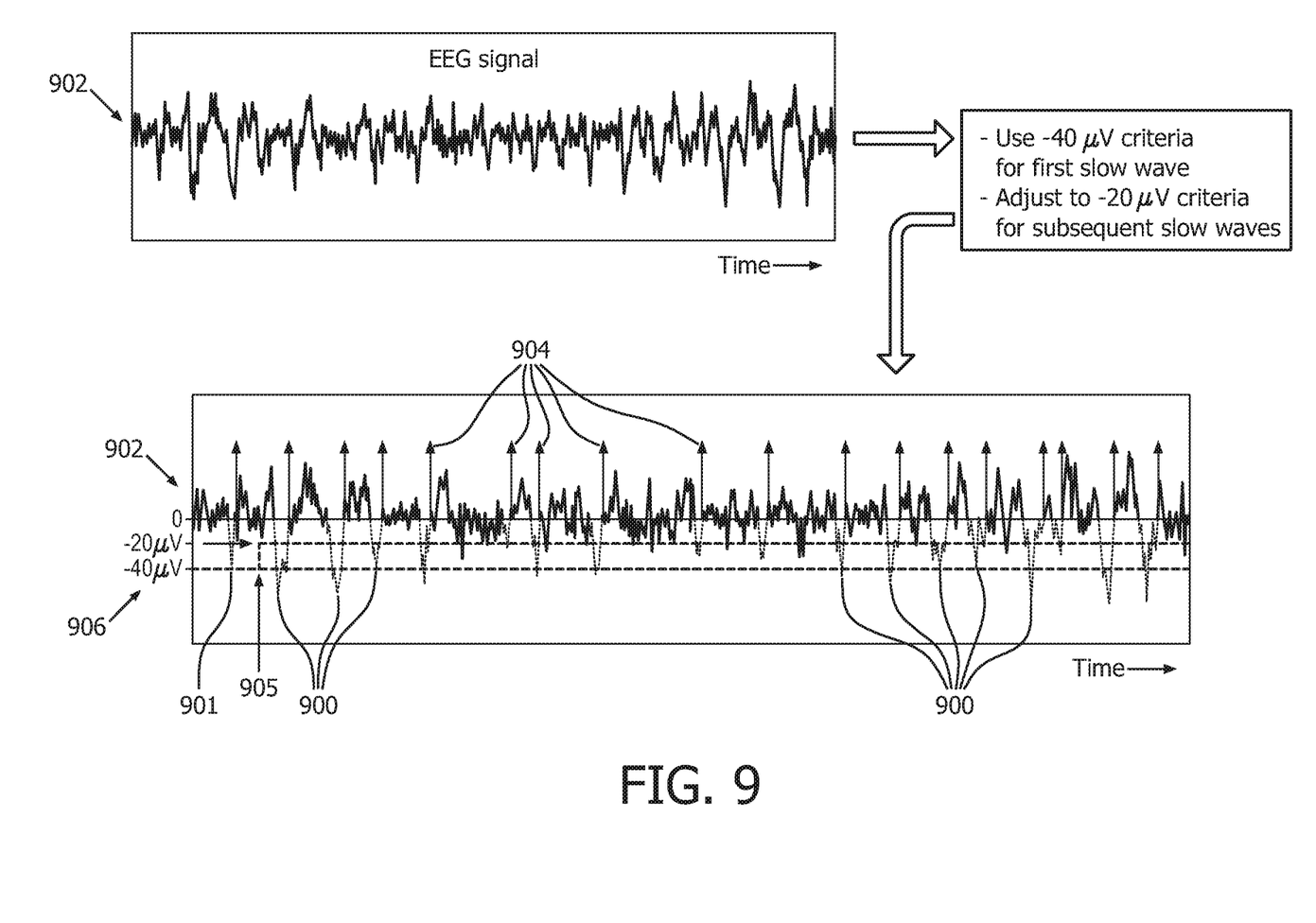
FIG. 9 illustrates detecting slow waves in an EEG voltage signal and corresponding delivery of auditory tones using adjusted negative peak voltage criteria.

FIG. 8 illustrates detecting slow waves 800 in an EEG voltage signal 802 and corresponding delivery of auditory tones 804 using static, unchanging negative peak voltage criteria 806 of −40 μV. FIG. 9 illustrates detecting slow waves 900 in an EEG voltage signal 902 and corresponding delivery of auditory tones 904 using adjusted negative peak voltage criteria 906 of −20 μV. In FIG. 9, negative voltage peak criteria 906 is adjusted 905 from −40 μV to −20 μV after detection of a first slow wave 901. Visually comparing FIG. 9 to FIG. 8 (both figures have the same time scale) shows several more tones delivered in FIG. 9 compared to FIG. 8.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24. Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 10:
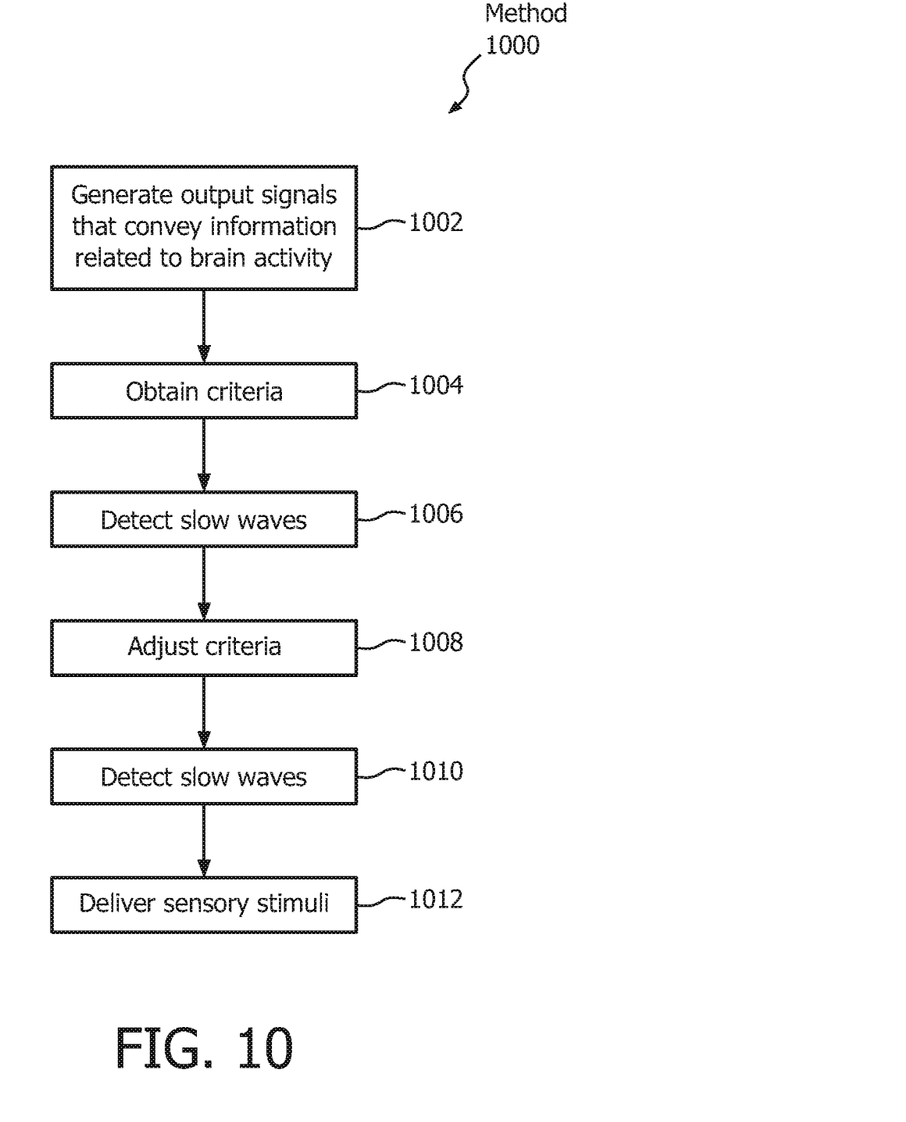
FIG. 10 illustrates a method for adjusting criteria for detecting slow waves in a subject and delivering sensory stimuli with a timing that corresponds to detected slow waves with an adjustment system.

FIG. 10 illustrates a method 1000 for adjusting criteria for detecting slow waves in a subject and delivering sensory stimuli with a timing that corresponds to detected slow waves with an adjustment system. The adjustment system comprises one or more sensory stimulators, one or more sensors, one or more physical computer processors, and/or other components. The one or more physical computer processors are configured to execute computer program components. The computer program components comprise a criteria component, a slow wave component, an adjustment component, a control component, and/or other components. The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 10 and described below is not intended to be limiting.

In some embodiments, method 1000 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1000 in response to instructions stored electronically on an electronic storage medium. The one or more processing devices may include one or more devices configured through hardware, firmware, and/or software to be specifically designed for execution of one or more of the operations of method 1000.

At an operation 1002, output signals conveying information related to brain activity are generated. In some embodiments, the output signals are generated during a sleep session of the subject. In some embodiments, the system may be configured to generate an EEG based on the output signals. In some embodiments, operation 1002 is performed by one or more sensors the same as or similar to sensors 18 (shown in FIG. 1 and described herein).

At an operation 1004, criteria for detecting whether slow waves are present in the subject are obtained. In some embodiments, operation 1004 is performed by a processor component the same as or similar to criteria component 30 (shown in FIG. 1 and described herein).

At an operation 1006, slow wave sleep is detected in the subject. Detecting slow wave sleep includes detecting a first slow wave based on the output signals and the obtained criteria. In some embodiments, operation 1006 is performed by a processor component the same as or similar to slow wave component 32 (shown in FIG. 1 and described herein).

At an operation 1008, the obtained criteria are adjusted to enhance detection of subsequent slow waves in the subject. In some embodiments, the criteria is adjusted based on one or more of predetermined threshold levels for an EEG signal, a sleep cycle of the subject, delta activity RMS, an amplitude of one or more previously detected slow waves, and/or other information. In some embodiments, operation 1008 is performed by a processor component the same as or similar to adjustment component 34 (shown in FIG. 1 and described herein).

At an operation 1010, a second slow wave is detected based on the output signals and the adjusted criteria. In some embodiments, the second slow wave immediately follows the first slow wave during a first sleep cycle of the subject. In some embodiments, the first slow wave is a leading slow wave in a first sleep cycle and the second slow wave is a leading slow wave in a second sleep cycle of the subject. In some embodiments, operation 1010 is performed by a processor component the same as or similar to slow wave component 32 (shown in FIG. 1 and described herein).

At an operation 1012, the one or more sensory stimulators are controlled to deliver sensory stimulation with a timing that corresponds to detection of the first slow wave and detection of the second slow wave. In some embodiments, operation 1012 includes controlling the one or more sensory stimulators to deliver time-out stimulation responsive to a time-out time after detection of the first slow wave and/or the second slow wave elapsing. In some embodiments, operation 1012 is performed by a processor component the same as or similar to control component 36 (shown in FIG. 1 and described herein).

The description of two individual slow waves is not intended to be limiting. The two described slow waves are intended to be representative of any number of slow waves that occur in the subject. In some embodiments, the operations described above are repeated in an ongoing manner (e.g., for multiple slow waves, multiple sleep cycles, etc.) during a sleep session of the subject. For example, the criteria may be adjusted following every individual detection of a slow wave in a series of consecutive slow waves. The criteria may be adjusted again during other series of slow waves that occur during later sleep cycles of the subject during the sleep session.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to adjust criteria for detecting slow waves in a subject and deliver sensory stimuli with a timing that corresponds to the detected slow waves, the system comprising:
one or more sensory stimulators configured to provide the sensory stimuli to the subject during a sleep session;
one or more sensors configured to generate output signals conveying information related to brain activity of the subject; and
one or more physical computer processors configured by computer readable instructions to:
obtain criteria for detecting whether the slow waves are present in the subject;
determine that the subject is in slow wave sleep by detecting a first slow wave based on the output signals and the obtained criteria;
adjust the obtained criteria to enhance detection of subsequent slow waves in the subject;
detect a second slow wave based on the output signals and the adjusted criteria, wherein the second slow wave immediately follows the first slow wave during an individual sleep cycle of the subject; and control the one or more sensory stimulators to deliver the sensory stimuli with a timing that corresponds to detection of the first slow wave and detection of the second slow wave.

2. The system of claim 1, wherein the one or more physical computer processors are further configured to cause the one or more sensory stimulators to deliver time-out stimulation responsive to a time-out time after detection of the first slow wave and/or the second slow wave elapsing.

3. The system of claim 1, wherein the one or more physical computer processors are further configured to adjust the criteria based on one or more of predetermined threshold levels for an electroencephalogram (EEG) signal, a sleep cycle of the subject, delta activity root mean square (RMS), or an amplitude of one or more previously detected slow waves.

4. A method for adjusting criteria for detecting slow waves in a subject with an adjustment system, the adjustment system comprising one or more sensory stimulators, one or more sensors, and one or more physical computer processors, the method comprising:
   generating, with the one or more sensors, output signals conveying information related to brain activity of the subject;
   obtaining, with the one or more physical computer processors, criteria for detecting whether the slow waves are present in the subject;
   determining, with the one or more physical computer processors, that the subject is in slow wave sleep by detecting a first slow wave based on the output signals and the obtained criteria;
   adjusting, with the one or more physical computer processors, the obtained criteria to enhance detection of subsequent slow waves in the subject;
   detecting, with the one or more physical computer processors, a second slow wave based on the output signals and the adjusted criteria, wherein the second slow wave immediately follows the first slow wave during an individual sleep cycle of the subject; and
   controlling, with the one or more physical computer processors, the one or more sensory stimulators to deliver the sensory stimuli with a timing that corresponds to detection of the first slow wave and detection of the second slow wave.

5. The method of claim 4, further comprising causing, with the one or more physical computer processors, the one or more sensory stimulators to deliver time-out stimulation responsive to a time-out time after detection of the first slow wave and/or the second slow wave elapsing.

6. The method of claim 4, further comprising adjusting the criteria based on one or more of predetermined threshold levels for an electroencephalogram (EEG) signal, a sleep cycle of the subject, delta activity root mean square (RMS), or an amplitude of one or more previously detected slow waves.

7. A system configured to adjust criteria for detecting slow waves in a subject and deliver sensory stimuli with a timing that corresponds to the detected slow waves, the system comprising:
   means for providing sensory stimuli to the subject during a sleep session;
   means for generating output signals conveying information related to brain activity of the subject;
   means for obtaining criteria for detecting whether the slow waves are present in the subject;
   means for determining that the subject is in slow wave sleep by detecting a first slow wave based on the output signals and the obtained criteria;
   means for adjusting the obtained criteria to enhance detection of subsequent slow waves in the subject;
   means for detecting a second slow wave based on the output signals and the adjusted criteria, wherein the second slow wave immediately follows the first slow wave during an individual sleep cycle of the subject; and
   means for controlling the means for providing sensory stimuli to deliver the sensory stimuli with a timing that corresponds to detection of the first slow wave and detection of the second slow wave.

8. The system of claim 7, further comprising means for causing the means for providing sensory stimuli to deliver time-out stimulation responsive to a time-out time after detection of the first slow wave and/or the second slow wave elapsing.

9. The system of claim 7, wherein the criteria are adjusted based on one or more of predetermined threshold levels for an electroencephalogram (EEG) signal, a sleep cycle of the subject, delta activity root mean square (RMS), or an amplitude of one or more previously detected slow waves.

* * * * *